United States Patent [19]

Harmer

[11] Patent Number: 5,277,772
[45] Date of Patent: Jan. 11, 1994

[54] CHEMICAL MODIFICATION OF SURFACES USING HETEROCYCLIC AZIDES

[75] Inventor: Mark A. Harmer, Wilmington, Del.

[73] Assignee: E. I. Du Pont de Nemours and Company, Wilmington, Del.

[21] Appl. No.: 692,083

[22] Filed: Apr. 26, 1991

[51] Int. Cl.$^5$ .............................................. C07D 201/00
[52] U.S. Cl. ................................. 264/157.69; 427/508
[58] Field of Search ............... 327/54.1, 472, 510, 327/508; 204/157.69, 157.70, 157.71

[56] References Cited

U.S. PATENT DOCUMENTS

| | | | |
|---|---|---|---|
| 2,875,092 | 2/1959 | Cline | 427/508 |
| 3,954,583 | 3/1985 | Lednicer et al. | 260/198 |
| 4,099,910 | 1/1985 | Herweh | 8/115.5 |
| 4,309,453 | 4/1987 | Reiner et al. | 427/54.1 |

FOREIGN PATENT DOCUMENTS

WO89/05329 4/1985 World Int. Prop. O.

OTHER PUBLICATIONS

F. Yamamoto et al., Journal of Polymer Science: Polymer Chemistry edition, vol. 16, 1897–1907 (1978).
He Mingbo et al., Polymer Degradation and Stability, 18, 321–328 (1987).
A. Hult et al., Macromolecules 18, 1804–1809 (1985).
E. W. Meijer et al., J. Am. Chem. Soc., 110, 7209–7210 (1988).
Hitoshi Kubota et al., Polymer Photochemistry 7 (1986), 379–387.
K. Kaji, Journal of Applied Polymer Science, vol. 32, 4405–4422 (1986).
Gerald Oster et al., Journal of Polymer Science vol. XXVI, Issue No. 113 (1957), 233–234.

*Primary Examiner*—John Niebling
*Assistant Examiner*—Cybille Delacroix-Muirheid

[57] ABSTRACT

The invention concerns a method for the chemical modification of a surface based on the reaction of photolytically generated reactive intermediates derived from azido heterocycles with said surface.

21 Claims, No Drawings

CHEMICAL MODIFICATION OF SURFACES USING HETEROCYCLIC AZIDES

BACKGROUND OF THE INVENTION

1. Field of the Invention

This invention concerns a method for the chemical modification of a surface based on the reaction of photolytically generated reactive intermediates derived from azido heterocycles with said surface.

2. Technical Background

Various methods for modification of surfaces are known. Radiation-induced grafting of moieties to polymeric surfaces has been disclosed. In some of these prior art processes, multiple stages are involved and reproducability may be a problem.

F. Yamamoto et al., Journal of Polymer Science: Polymer Chemistry edition, Vol 16, 1897–1907 (1978), discuss the grafting of methyl acrylate onto the surface of polyethylene film under the influence of high energy electrons.

He Mingbo et al., Polymer Degradation and Stability, 18, 321–328(1987) discuss the grafting of 2,2,6,6-tetramethyl-4-piperidinyl-methacrylate onto the surface of polypropylene under the influence of ultraviolet radiation.

A. Hult et al, Macromolecules 18, 1804–1809(1985), disclose a method for the surface modification of polymers that is based upon photoinitiated cationic polymerization under the influence of ultraviolet radiation.

Lednicer et al. U.S. Pat. No. 3,954,583 disclose a process for coating materials which are susceptible to interaction with an aromatic sulfonyl nitrene which involves contacting an aromatic sulfonylazide with said material and irradiating. The types of radiation employed are said to include ultraviolet, ultrasound and X-ray radiation.

E. W. Meijer et al., J. Am. Chem. Soc., 110, 7209–7210(1988), discuss the ultraviolet light induced polymerization of phenyl azide and a series of substituted phenyl azides. He proposes a reaction mechanism involving formation of a nitrene followed by a ring expanding nitrene insertion reaction to form a seven-membered ring compound (an azepine), which then polymerizes. The polymerization can be carried out in an image wise fashion if the irradiation is performed through a photomask. There is no indication nor suggestion that azides other than phenyl azides, least of all heterocyclic azides, would react and polymerize in a similar fashion. There is no indication nor suggestion that surfaces other than silica might be suitable substrates for the formation of photopolymerized phenyl azide films.

Reiner et al., U.S. Pat. No. 4,309,453 disclose a process for the covalent surface modification of a macromolecular substance comprising applying a solution of an organic monomeric compound having a hydrophobic linear chain having at least one azide or diazo group at one end of said monomeric compound and having at least one hydrophilic, hydrophobic, oleophobic and/or ionic group at the other end of said compound, to the surface and then photochemically activating said molecule to convert said compound to a nitrene or a carbene. One of the compounds specifically disclosed is a para substituted alkyl phenyl azide. There is no indication nor suggestion that azides other than alkyl azides and the disclosed phenyl azide, least of all heterocyclic azides, would react in a similar fashion.

It is known in the art that different classes of azides, for example heterocyclic azides, may undergo different types of reactions. Different yields of the various types of possible products are obtained. See, Azides and Nitrenes, E. F. V. Scriven, Editor, Academic Press, 1984.

SUMMARY OF THE INVENTION

The object of the present invention is to provide a surface modification process that can be applied to a wide range of surfaces.

This method comprises the photoactivation of an azido heterocyclic compound, such as 3-azidopyridine, 4-azidopyridine or 3-azidothiophene, in the presence of the surface to be modified to generate a reactive intermediate, followed by the interaction of the photogenerated reactive intermediate with the surface to form the modified surface.

This invention also provides a method for the chemical modification of surfaces in an image wise fashion which method comprises the photoactivation, in an image wise fashion, of an azido heterocyclic compound, such as 3-azidopyridine, 4-azidopyridine or 3-azidothiophene, in the presence of the surface to be modified, to generate a reactive intermediate, followed by the interaction of the photogenerated reactive intermediate with the surface in an image wise fashion to form the image wise fashion modified surface.

DETAILED DESCRIPTION OF THE INVENTION

The invention concerns a method for the chemical modification of a surface based on the reaction of photolytically generated reactive intermediates derived from azido heterocycles with said surface. Heterocyclic azides are applied to surfaces of substrates, either in a gas phase or in a liquid phase, in the substantial absence of air and water, then photolysed at or near the surface. On photolysis, a highly reactive nitrene is generated which chemically binds to the surface or to surface groups, for example hydroxyl —OH, and also various organic functional groups on the surface, resulting in a stable film on the surface of the substrate. By photolysis through a mask, lithographic images can be produced.

This method can be applied to a wide variety of surfaces including, but not limited to, glass, aluminum, polyethylene, polyester, polyimide, various fluoropolymers and various fibers. The method is generally applicable to modifying the surfaces and the surface properties of different classes of materials containing —OH, —C—H, —N—H and —C—F on the surface, such as polyethylene, Kapton ® polyimide, polytetrafluoroethylene, copolymers of tetrafluoroethylene(TFE), an oxide surface that may contain —OH groups at the surface, including silica glass (quartz or Pyrex ®), tin oxide, borosilicates, and any other standard glass substrates. The net result of such modification is that the surface takes on the character of the heterocyclic compound, for example, pyridine. Substituents on the heterocyclic compound can be varied, which will, in turn, further modify the properties of the surface. The process of the present invention is a procedure for modifying a wide range of surfaces with a wide range of heterocyclic azides.

The surface of fibers can also be treated to modify its properties by the process of the present invention. Fibers such as those drawn from polyester can be surface coated with the selected heterocyclic azide described above, using any surface coating technique, for example dipping, spraying, padding, brushing or vapor transfer. The surface coated fiber is then subjected to photolysis, according to the present invention, to form the surface modified substrate. The fibrous material can be in the form of individual fibers or in the form of woven goods, knitted goods, rope or tow.

The photolytic treatment is carried out in the absence of an atmosphere that leads to side reactions. It is preferable to carry out the reaction in the absence of air and water, although the reaction will proceed in their presence, but at lower efficiencies due to competing reactions. The atmosphere may consist of the vapors of the utilized heterocyclic azide or an inert gas or a mixture of the two.

Photolysis time may be varied to cause a variation in the thickness of the film obtained. Using the procedure, as described in Example 1, the photolysis time has been varied from 15 seconds to 10 minutes. Over this time there is a gradual change in film coverage from light yellow to a dark yellow brown.

A number of different substrate materials have been modified using a procedure similar to that in Example 1, below. In all cases the treated surface is rendered more hydrophilic than the non-treated surface, as determined by water contact angle measurements. See Table 1.

TABLE 1

| Substrate | Contact Angle Before | Contact Angle After |
| --- | --- | --- |
| polyethylene | 92 deg | 65 deg |
| TFE/hexafluoro propylene copolymer | 104 | 61 |
| TFE/ethylene copolymer | 92 | 56 |
| TFE/perfluoropropyl vinyl ether copolymer | 96 | 59 |

The film produced by the process of the present invention has various applications. For example, improved adhesion of metals has been achieved on photomodified surfaces. A polyethylene sample, photomodified by a method analogous to the method of Example 1, was coated with gold by sputtering gold onto the surface to give a gold film 0.1 micron thick. The gold adhered well enough to withstand a Scotch ® brand cellophane tape peel test. If gold is sputtered onto a non-modified polyethylene surface, most of the gold is removed in the peel test.

The photomodified surfaces that result from an azido pyridine show acid base properties. The 3-azidopyridine surface can be protonated by treatment with 0.5M sulfuric acid. If said surface is acid treated and then washed with water to remove residual acid, the water contact angle is further reduced from that shown in Table 1, above. This is consistent with protonation of the pyridine functionalities on the surface. For a particular sample of photomodified polyethylene, the water contact angle was 75 degrees. After treatment with sulfuric acid, the water contact angle was reduced to 40 degrees. The surface shows acid base character and when it is protonated, the films can be used to absorb negatively charged molecules. For example, bromophenol blue has been absorbed onto the acid treated surface and binds tightly. Redox active molecules, for example negatively charged ferrocyanide or hexachloroiridate can be bound to a tin oxide surface that has been photomodified with pyridines. This surface can now be employed as a chemically modified electrode for use in the electronics industry or for catalysis. See Acc. Chem. Res. 1980, 13, 135–141.

Particularly useful in the process of the present invention are those heterocyclic azides where the azide is directly bound to the hetero-ring, for example 3 and 4-azidopyridine, 3-azidothiophene and 3-azidopyrole. The azide may be a liquid or a solid at room temperature. The heterocycle may, in addition, have functional groups attached to the ring for example, 3-azidopyrine with various R groups in the 5-position such as —COOH, OH, —NH$_2$, —CHO, —SO$_3$H, —COCl, —O—alkyl, or O-substitutes alkyl where a range of organic functional groups are present on the alkyl group. The preferred embodiments are those compounds which possess no substituents other than hydrogen directly adjacent to the azide group. Also included in the present invention are heterocyclic azides where more than one aromatic ring is present, for example, 3-azidoquinoline and related compounds.

EXAMPLES

EXAMPLE 1

Modification of Quartz Substrate Using Vaporous 3-Azidopyridine 0.2 g of 3-azidopyridine was placed in a quartz vessel which contained a quartz substrate of dimensions (1.5×2.5×0.1 cm). The substrate was suspended such that its surface was perpendicular to a light source. The light source used was a Xe-Hg lamp (100 watts), water cooled without filters.

The vessel containing the 3-azidopyridine was cooled with liquid nitrogen and the vessel was evacuated under a vacuum of about $1\times10^{-6}$ Torr. Whilst still under vacuum a stopcock to the flask was closed. The flask and contents were allowed to warm up to room temperature ensuring that the vapor pressure in the flask was 3-azidopyridine and that air had been essentially excluded.

The liquid 3-azidopyridine remaining at the bottom of the flask was shielded from direct light by aluminum foil. The substrate and vapor of the 3-azidopyridine was then photolysed directly with light from the Xe-Hg lamp for 5 min. The lamp was situated 4 cm from the quartz vessel. An even light brown-yellow coating formed on the glass leading to photomodification of the glass surface. The glass and coating was then removed and washed sequentially with hexane, tetrahydrofuran and acetone leaving a stable surface coating on the quartz glass. The film thickness is of the order of a micron as measured by scanning electron microscopy.

Using the above procedure, films were photolytically generated using 4-azidopyridine and 3-azidothiopene.

EXAMPLE 2

Modification of Quartz Substrate Using Liquid 3-Azidopyridine

A thin film of liquid 3-azidopyridine (0.05 ml) was applied to a quartz substrate and the substrate with 3-azidopyridine coating was placed in a quartz glass vessel with a flow of nitrogen purging through the vessel. The substrate and 3-azidopyridine were photolysed for 5 min after which time the film became dark brown. The substrate and coating was washed with solvent to leave a surface coating attached to the quartz substrate.

Using the above procedure, films were photolytically generated using 4-azidopyridine and 3-azidothiophene.

EXAMPLE 3

Modification of Quartz Substrate Using Vaporous 3-Azidopyridine

A slow stream of nitrogen was passed through liquid 3-azidopyridine generating a gas phase composition of 3-azidopyridine and nitrogen. This gas flow mixture was passed over the surface of a quartz substrate whilst the substrate was being photolysed with the Xe-Hg lamp. The substrate is maintained entirely in the nitrogen/3-azidopyridine atmosphere. After 5 min photolysis an even thin brown coating was formed on the glass which remained after extensive washing with acetone and hexane.

Using the above procedure, films were photolytically generated using 4-azidopyridine and 3-azidothiopene.

EXAMPLE 4

Image-Wise Film Formation with 3-Azidopyridine

3-Azidopyridine was placed on a glass substrate as in Example 2 and a conventional photomask was placed on the top of this and the whole assembly placed in a quartz vessel and placed under a nitrogen atmosphere. Light from a Xe-Hg lamp was then directed at the assembly for 15 min. The photomask was then removed and the substrate and coating were washed. A very well defined image was obtained where the light had passed through the mask. Lines as small as 5 microns wide by about 0.5 microns thick have been generated by this method.

EXAMPLE 5

3-Azidopyridine was placed on a tin oxide substrate and photolysed for 15 minutes. The substrate was then washed in acetone/water. This assembly was then placed in 0.5 molar HCl for one hour. This assembly was then subjected to anion exchange with ferrocyanide ion, so as to modify the surface. Electrochemical measurements showed that the redox active couple is bound to the surface showing a well defined oxidation and reduction peak at a potential of 0.31 volts compared to a silver/silver chloride reference electrode.

EXAMPLE 6

Ferricyanide Modified Tin Oxide Electrodes

A tin oxide electrode of dimensions 0.5 cm×3.0 cm×0.1 cm wide was placed in a quartz vessel. 0.1 g of 3-azidopyridine was added to the vessel. The cell was then cooled in liquid nitrogen and then the vessel was subjected to a vacuum for 30 minutes. The vessel was then sealed by turning a stopcock and the vessel allowed to warm up to room temperature. The vessel and contents were then placed in a Rayonet photochemical reactor and the vessel and contents were then exposed to a light of 254 nm for 30 minutes. The conducting tin electrode was removed and washed with acetone and water. The film adhered well to the surface. The modified electrode was then immersed in 0.05M sulfuric acid for 15 minutes and then rinsed in water. The modified electrode was then treated by immersing in 2 mls of water into which 0.05 g of potassium ferricyanide had been dissolved. The electrode was left for 15 minutes and then removed and washed in water.

Electrochemical measurements confirmed that the ferricyanide redox couple was attached to the surface, using cyclic voltammetry. An oxidation-reduction peak was found at 0.31 volts versus the silver/silver chloride reference electrode. The behavior was consistent with a surface bound species. Without the acid treatment step, none of the ferricyanide became bound to the tin oxide.

EXAMPLE 7

Photomodification of Polyethylene

A piece of polyethylene was placed in the photochemical reaction vessel with 0.1 g of 3-azidopyridine. The vessel was cooled to liquid nitrogen temperature, evacuated and then sealed. After warming the vessel up to room temperature, the vessel and contents were photolysed for 10 minutes, after which time an even yellow/yellow-brown coating was formed on the polyethylene which was shown to be stable to washing with acetone and water. The size of the modified polyethylene was 2 sq, cm.

Although preferred embodiments of the invention have been described hereinabove, it is to be understood that there is no intention to limit the invention to the precise constructions herein disclosed, and it is to be further understood that the right is reserved to all changes coming within the scope of the invention as defined by the appended claims.

I claim:

1. A method for the chemical modification of a surface which method comprises the photoactivation of an azido heterocyclic compound, containing one or more aromatic rings, in the presence of the surface, to generate a reactive intermediate, followed by the interaction of the photogenerated reactive intermediate with the surface to form a modified surface, wherein said process is carried on in the substantial absence of air and water.

2. The method of claim 1 wherein the azido heterocyclic compound has an azide directly bound to the hetero-ring.

3. The method of claim 2 wherein the azido heterocyclic compound is selected from 3-azidopyridine, 4-azidopyridine, 3-azidopyrole and 3-azidothiophene.

4. The method of claim 1 wherein the azido heterocyclic compound is a liquid at room temperature.

5. The method of claim 1 wherein the azido heterocyclic compound is a solid at room temperature.

6. The method of claim 1 wherein the heterocyclic part of the azido heterocyclic compound has one or more functional groups attached to the ring.

7. The method of claim 6 wherein the azido heterocyclic compound has no substituents other than hydrogen directly adjacent to the azide group.

8. The method of claim 1 wherein the surface to be modified is selected from glass, aluminum, polyethylene, polyester, polyimide, a fluoropolymer, and a fiber.

9. The method of claim 1 wherein the surface to be modified has a —OH, —C—H, —N—H or —C—F on the surface.

10. A method for the chemical modification of surfaces in an image wise fashion which method comprises the photoactivation, in an image wise fashion, of an azido heterocyclic compound, containing one or more aromatic rings, in the presence of the surface to generate a reactive intermediate, followed by the interaction of the photogenerated reactive intermediate with the surface in an image wise fashion to form the image wise fashion modified surface, wherein said process is carried on in the substantial absence of air and water.

11. The method of claim 10 wherein the azido heterocyclic compound has an azide directly bound to the hetero-ring.

12. The method of claim 11 wherein the azido heterocyclic compound is selected from 3-azidopyridine, 4-azidopyridine, 3-azidopyrole and 3-azidothiophene.

13. The method of claim 10 wherein the azido heterocyclic compound is a liquid at room temperature.

14. The method of claim 10 wherein the azido heterocyclic compound is a solid at room temperature.

15. The method of claim 10 wherein the heterocyclic part of the azido heterocyclic compound has one or more functional groups attached to the ring.

16. The method of claim 10 wherein the azido heterocyclic compound has no substituents other than hydrogen directly adjacent to the azide group.

17. The method of claim 10 wherein the surface to be modified is selected from glass, aluminum, polyethylene, polyester, polyimide, a fluoropolymer, and a fiber.

18. The method of claim 10 wherein the surface to be modified has a —OH, —C—H, —N—H or —C—F on the surface.

19. A method for the chemical modification of a surface comprising the photoactivation of an azido heterocyclic compound, containing one or more aromatic rings, in the presence of the surface to be modified so as to cause the azido heterocyclic compound to modify the surface, wherein said process is carried out in the substantial absence of air and water.

20. The method of claim 19 wherein the surface to be modified is a fluoropolymer.

21. The method of claim 1 wherein the surface to be modified is a fluoropolymer.

* * * * *